United States Patent [19]

Keve et al.

[11] 4,424,223

[45] Jan. 3, 1984

[54] POLYCYCLIC COMPOUNDS CONTAINING A DOUBLE BOND IN THE D-RING PHARMACEUTICAL COMPOSITIONS CONTAINING THEM, AND METHODS OF TREATING PSORIASIS WITH THEM

[75] Inventors: Tibor Keve; Béla Zsadon; György Fekete; Csaba Lorincz, all of Budapest; János Galambos, Erd; Máriá Zájer née Balazs, Budapest; Lilla Forgách, Budapest; Egon Karpati, Budapest; Arpad Kiràly, Budapest; Gyongyver Király née Soós, Budapest; László Szporny, Budapest; Bela Rosdy, Budapest, all of Hungary

[73] Assignee: Richter Gedeon Vegyészeti Gyar RT, Budapest, Hungary

[21] Appl. No.: 345,630

[22] Filed: Feb. 4, 1982

[30] Foreign Application Priority Data

Feb. 11, 1981 [HU] Hungary ............................ 321

[51] Int. Cl.$^3$ .................. A61K 31/435; C07D 461/00
[52] U.S. Cl. ........................................ 424/256; 546/51
[58] Field of Search ............................ 546/51; 424/256

[56] References Cited

U.S. PATENT DOCUMENTS

| | | | |
|---|---|---|---|
| 4,065,458 | 12/1977 | Lörincz et al. | 424/256 X |
| 4,108,996 | 8/1978 | Lörincz et al. | 424/256 |
| 4,285,949 | 8/1981 | Hannart | 424/256 |
| 4,328,231 | 5/1982 | Zajer nee Balazs et al. | 424/256 |

FOREIGN PATENT DOCUMENTS 2462909  2/1981  France .

OTHER PUBLICATIONS

Bruneton, et al., Chemical Abstracts, vol. 83, 10551h (1975).
Bruneton, et al., Chemical Abstracts, vol. 79, 50705k (1973).

Primary Examiner—Diana G. Rivers
Attorney, Agent, or Firm—Karl F. Ross; Herbert Dubno

[57] ABSTRACT

The invention relates to the new 17,18-dehydro-apovincaminol-3',4',5'-trimethoxy-benzoate of formula (I)

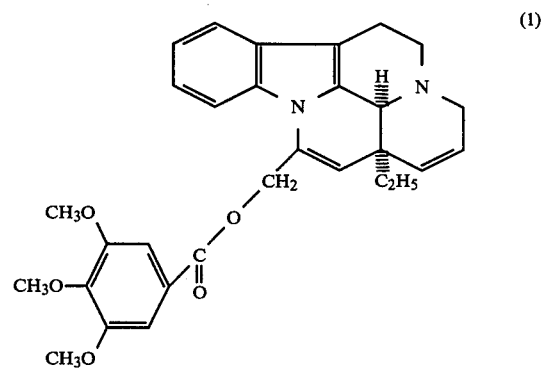

and acid addition salts thereof.

According to another aspect of the invention there is provided a process for the preparation of these new compounds. Still another aspect of the invention is a pharmaceutical composition for treating psoriasis.

6 Claims, No Drawings

POLYCYCLIC COMPOUNDS CONTAINING A DOUBLE BOND IN THE D-RING PHARMACEUTICAL COMPOSITIONS CONTAINING THEM, AND METHODS OF TREATING PSORIASIS WITH THEM

The invention relates to a new polycyclic compound containing a double bond in the D-ring. More particularly, the invention concerns the new 17,18-dehydro-apovincaminol-3',4',5'-trimethoxy-benzoate of the formula (I)

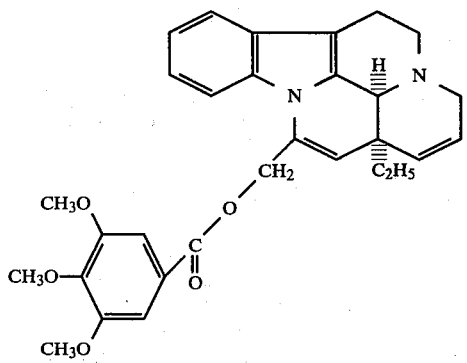

and acid addition salts thereof. According to another aspect of the invention there is provided a method for preparing 17,18-dehydro-apovincaminol-3',4',5'-trimethoxy-benzoate and acid addition salts thereof. The transformation vincadifformine→vincamone→vicamine has been discussed in the art.

Kutney et al. [J. Am. Chem. Soc. 93(1), 255 (1971)] describe, interalia, the transformation tabersonine→17,18-dehydro-vincamine. A synthesis based on the latter conversion is disclosed in the Belgian Patent Specification No. 818.144.

The known starting compounds have a vascotropin activity. The compound according to the invention can be prepared by treating compounds of formula

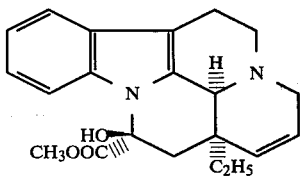

and/or (IVb)

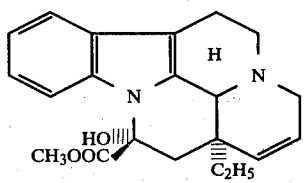

with a suitable dehydrating agent, reducing the obtained compound of formula (III)

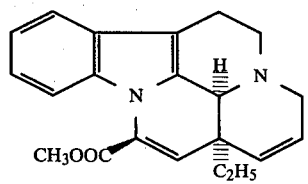

with a selective reducing agent, preferably a complex metal hydride and then reacting the resulting compound of formula (II)

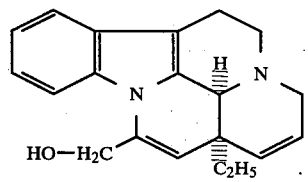

obtained with 3,4,5-trimethoxy-benzoic acid or a derivative thereof capable of acylation and of desired, converting the compound of formula (I) obtained into an acid addition salt thereof.

The new compound of formula (I) and acid addition salts thereof inhibit phosphodiesterase enzyme activity and are particularly suitable for treating skin diseases accompanied by pathological cell proliferation. The compounds have also prophylactic effect.

Skin diseases accompanied by a pathological proliferation of epidermis are relatively frequent and involve several percent of population. Diseases of this kind include psoriasis.

Since many skin diseases accompanied by a pathological cell proliferation do not occur on animals, e.g. psoriasis, the anti-psoriatic activity of the compounds can only be demonstrated in tests indirectly.

Voorhees et al. [Arch. Derm. 104, 359–365 (1971)] established that the pathological proliferation is accompanied by the decrease of the level of cyclic adenozine monophosphate (c-AMP). As it is well known, c-AMP is produced by adenyl cyclase and is decomposed by phosphodiesterase. Voorhees successfully influenced psoriasis by agents stimulating the activity of adenyl cyclase (e.g. norepinephrine) or inhibiting the activity of phosphodiesterase (e.g. papaverine).

When planning our model experiments we set out from the assumption that the inverse of Voorhees's statement is also true, i.e. if a compound inhibits the activity of phosphodiesterase, this indirectly renders it probable that said compound is suitable for treating psoriasis or other skin diseases accompanied by a patological cell proliferation. This assumption has been verified, i.e. the compound showing in vitro a phosphodiesterase inhibitory activity proved effective in clinical treatment of psoriasis.

The model experiments were performed by means of phosphodiesterase isolated from animal tissues (rat brain, cattle brain, cattle heart). The enzyme was isolated by the technique of J. Schröder and H. V. Richenberg [Biochem. Biophys. Acta 302, 50 (1973)] whereupon the phosphodiesterase isolated was purified according to the method of J. G. Hardman and E. W. Sutherland [J. Biol. Chem. 240, 3704 (1965)] and the activity of the purified enzyme was measured by a radioisotopic method developed by G. Pöch, in the presence of an excess amount of c-AMP tricium-labeled (10.1 mmoles of a c-AMP substrate containing 2.59 K Bq of 3H-c-AMP), in an incubator. The measurement was first carried out without the inhibitory substance and then in the presence of 17,18-dehydro-apivincaminol-3',4',5'-trimethoxy-benzoate as an inhibitor agent, after an incubation time of 20 minutes [N.S. Arch. Pharmacol. 268, 272 (1971)]. From the test compound a 1 mmole stock solution was prepared with aqueous hydrochloric acid solution and different amounts of the stock solution were added to the enzyme preparates corresponding to $5 \times 10^{-6}$, $1 \times 10^{-5}$ and $5 \times 10^{-5}$ mole/lit. of the test compound. A solution of papaverine used as reference compound is added to the enzyme preparate in an analogous manner.

The activity of the solutions containing 17,18-dehydro-apovincaminol-3',4',5'-trimethoxy-benzoate and papaverine was expressed in percents of the control (enzyme solution without any inhibitory substance, 100%). The results obtained on an enzyme isolated from rat brain are as follows:

| Test compound (enzyme inhibitor) | The effect of a $5 \times 10^{-6}$ $1 \times 10^{-5}$ $5 \times 10^{-5}$ mole/lit. concentration of the test compound on enzyme activity in % of the control | | |
|---|---|---|---|
| 17,18-dehydro-apovincaminol-3',4',5'-trimethoxy-benzoate.HCl | 84.7 | 40.7 | 38.6 |
| papaverine.HCl | 91.2 | 89.7 | 60.5 |

The tests on an enzyme isolated from cattle brain and cattle heart, resp. were carried out in an analogous way. On the basis of the results obtained the enzyme activity was plotted against the logarithm of the concentration of enzyme inhibitor (μmoles) and from the curve the inhibitor concentration, which resulted in a 50% decrease of enzyme activity was read off ($I_{50}$). The results obtained are shown in the following table:

| Test compound | $I_{50}$ (μmoles) on phosphodiesterase isolated from | | |
|---|---|---|---|
| | cattle brain | cattle heart | rat brain |
| 17,18-dehydro-apovincaminol-3',4',5'-trimethoxy-benzoate.HCl | 15 | 3 | 10 |
| Papaverine.HCl | 90 | 50 | 70 |

The results set forth in the above table clearly show that the new compound according to the invention on an enzyme isolated from cattle brain was 6-times, on an enzyme isolated from cattle heart 18-times and on an enzyme isolated from rat brain 7-times more so effective than papaverine used as reference substance.

The first clinical tests were carried out with preparations for topical use, e.g. ointments, creams, solutions, tinctures, pastes, aerosols, etc. containing the new compound according to the invention as an active ingredient. More particularly, creams containing 2%, 1%, 0.5%, 0.25% and 1.1%, resp. of 17,18-dehydro-apovincaminol-3',4',5'-trimethoxy-benzoate were employed.

Clinical tests were performed on patients suffering from psoriasis. During the tests the patients have not received and systemic, e.g. immunosuppressive, cytostatic or glucocorticoid treatment for their basic disease.

Groups of 5 were examined by the so-called plaque method. One side of symmetrical skin lesions was treated by a creme containing the active ingredient in the desired concentration, while on the other side a placebo was applied. The remaining psoriatic sites on the skin were subjected to other topical treatments for example with ointments containing flumethasone pivalate and salicylic acid, as active ingredient, which are widely used for the treatment of psoriasis.

The tests were started with creams having a higher active ingredient concentration and then further patients were treated with preparations containing the smallest effective active ingredient concentration. The skin was treated 2 to 3-times a day until the symptoms disappeared or were considerably improved (1 to 6 weeks).

The efficiency was evaluated upon observing three symptoms: inflammation, infiltration and desquamation (peeling). The intensity of the symptoms was qualified by scores between 0 and 3. The total number of scores served as a measure of the reduction of symptoms. The results were evaluated by methods of mathematical statistics. During the treatment undesirable side effects have never been observed.

The results are shown in the following table.
0 = no symptom,
1 = moderate symptoms,
2 = strong symptoms
3 = very strong symptoms.

Evaluations were made before the treatment (I), after a one-week treatment (II) and after a two-week treatment (III). The results set forth in the following table are the average number of scores (total number of scores/number of patient) for creams containing 2% of active ingredient.

| | Average number of scores | | | | | | | | |
|---|---|---|---|---|---|---|---|---|---|
| | Infiltration | | | Inflammation | | | Desquamation | | |
| Active ingredient | I | II | III | I | II | III | I | II | III |
| 17,18-dehydro-apovincaminol-3',4',5'-trimethoxy-benzoate | 2.6, | 1.6, | 0.6, | 2.8, | 2.2, | 1.6, | 2.0, | 0.8, | 0.2, |

The test unambiguously proved that the compositions can successfully be used for treating psoriasis. No side effects were observed.

According to an aspect of the invention there is provided a process for preparing new 17,18-dehydro-apovincaminol-3',4',5'-trimethoxy-benzoate of the formula (I)

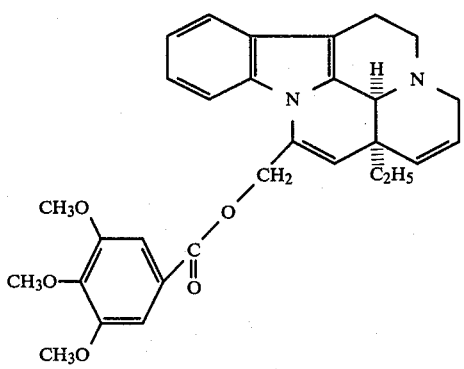

(I)

and acid addition salts thereof by
(a₁) treating compounds of the formula (IVa)

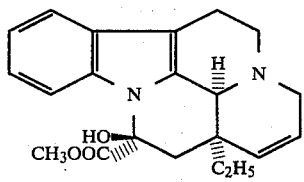

(IVa)

and/or (IVb)

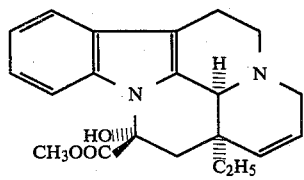

(IVb)

with a suitable dehydrating agent, reducing the resulting new compound of the formula (III)

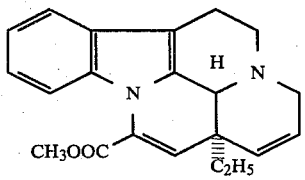

(III)

obtained by a selective reducing agent, preferably a complex metal hydride and then reacting the new compound of the formula (II)

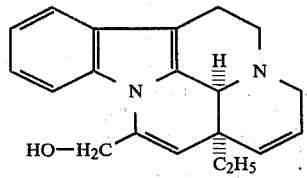

(II)

obtained with 3,4,5-trimethoxy-benzoic acid or a derivative thereof capable of acylation and if desired, converting the compound of the formula (I) obtained into an acid addition salt thereof; or (a₂) reacting the new compound of formula (III) with a selective reducing agent, preferably a complex metal hydride and reacting the new compound of formula (II) obtained with 3,4,5-trimethoxy-benzoic acid or a derivative thereof capable of acylation and if desired, converting the compound of formula (I) obtained into an acid addition salt thereof; or (a₃) reacting the new compound of formula (II) with 3,4,5-trimethoxy-benzoic acid or a derivative thereof capable of acylation and if desired, converting the compound of formula (I) obtained into an acid addition salt thereof.

According to another aspect of the invention there are provided pharmaceutical compositions having a phosphodiesterase inhibiting activity, in particular for treating and prophylaxis of skin diseases accompanied by a pathological cell proliferation which comprise as active ingredient a pharmaceutically effective amount of the compound of formula (I) or a pharmaceutically acceptable acid addition salt thereof with at least one pharmaceutically inert carrier or diluent and optionally further, pharmaceutically active substances.

According to the invention the new compound of formula (I) is prepared from the known compound(s) of formula (IVa) and/or (IVb) which are treated with a dehydrating agent. As a dehydrating agent for example sulfuric acid, Lewis acid, formic acid, a mixture of formic acid and a lower aliphatic carboxylic acid halide, acetic anhydride or p-toluene-sulfonic acid may be employed. The reaction is preferably carried out in the presence of an organic solvent, preferably a chlorinated hydrocarbon. The compound of formula (III) obtained as a result of this reaction does not contain a centre of asymmetry in the 14-position any more.

The compound of formula (III) obtained is then reacted with a selective reducing agent, preferably a complex metal hydride. For this purpose for example sodium dihydro-bis(2-methoxyethoxy)aluminate (Redal), lithiumaluminum hydride, etc. can be used. The reaction is performed in the presence of an organic solvent, preferably benzene or a homologue thereof or an ether.

The reduction results in the compound of formula (II), which is then reacted with 3,4,5-trimethoxy-benzoic acid or a derivative thereof capable of acylation.

Acylation is accomplished in the presence of an organic solvent, preferably benzene or a homolog thereof, chlorinated hydrocarbons or aliphatic ketons or pyridine. If the reaction is carried out with a 3,4,5-trimethoxy-benzoyl halide, an acid binding agent is added to the reaction mixture in an amount equivalent to the halogenic acid formed in the reaction or in a slight excess. As an acid binding agent for example alkali metal carbonates, alkali metal hydrocarbonates or organic basic amides, such as pyridine can be employed. If the reaction is carried out with 3,4,5-trimethoxy-benzoic acid, a catalytic amount of an acid, preferably hydrochloric acid or sulfuric acid or a carboxyl activator and/or a dehydrating agent is added to the reaction mixture. As a carboxyl activator for example halogenated phenols, preferably pentachlorophenol, as a dehydrating agent for example N,N'-dicyclohexyl-carbodiimide may be employed. The acylation is carried out at a temperature between −20° C. and the boiling temperature of the reaction mixture, preferably 20° C. and 60° C.

The product is isolated from the reaction mixture generally by extraction and/or evaporation.

If desired, the product obtained may be converted into an acid addition salt thereof. Preferred representatives of the inorganic acid addition salts are e.g. chlorohydrate, sulfate and phosphate salts. The preferred organic acid addition salts include the hydrogentartarate, succinate, citrate and ascorbate salts. The salts are prepared by adding an alcoholic, ethereal or acetone solution of the acid component to the product of formula (I). The preparation of salts is carried out at a pH between 3 and 6.

The pharmaceutical compositions according to the invention contain 0.1 to 8.0% by weight, preferably 0.2 to 2.0% by weight of active ingredient. The compositions optionally contain also further pharmaceutically active ingredient, e.g. antibiotics, cytostatic agent, prostaglandins, ditranol, salicyclic acid, tar, antiinflammatory agents, immunosuppressive agents, glucocorticoids and in case of parenteral administration local anaesthetics. As a glucocorticoid preferably triamcinolon acetonide is employed. The compositions preferably are finished as formulations suitable for topical, local application, a.g. creams, ointments, solutions, gelees, aerosols, aerosol foams, plasters, etc.

The active ingredient preferably is incorporated into a cream, easy to wash down.

Creams are prepared by dissolving the active ingredient in an alcoholic solvent, preferably propylene or dipropylene glycol or a mixture thereof with water and subsequently admixing the solution obtained with a well smearable skin compatible fatty phase.

The fatty phase may contain cetyl, stearyl, cetostearyl alcohol, paraffin oil, glycerine monostearate, etc.

The creams may further contain emulsifying agents, preferably polyoxyethylene-sorbitane monooleate or monostearate and preserving agents, e.g. various benzoic acid derivatives, preferably p-hydroxy-benzoic acid methyl ester.

The creams optionally contain 0.25 to 2.0% by weight of active ingredient, 45 to 50% by weight of glycol, 23 to 27% by weight of paraffine oil, 11 to 15% by weight of stearyl alcohol and further additives up to 100%.

The active ingredient may be formulated also as an ointment which cannot be washed down with water. In this case the active ingredient is directly incorporated into the fatty phase.

Solutions may be prepared for example with 20 to 40% by weight of propylene glycol or dipropylene glycol, 40 to 55% by weight of a 96% ethanol and distilled water up to 100%.

Aerosol formulations are prepared by adding a solution of the active ingredient in propylene glycol a fat, preferably isopropyl myristate and a suitable propellant, preferably freon.

An aerosol foam may for example be prepared by adding an alcoholic solution of the active ingredient to a mixture of 0.5 to 1.5% by weight of cetostearyl alcohol, 1 to 3% by weight of benzyl alcohol, 15 to 20% by weight of polyoxyethylene-sorbitane monooleate or monostearate and 25 to 30% by weight of water followed by the addition of freon.

For parenteral administration preferably injection solutions suitable for subcutaneous or intracutaneous administration are prepared. For this purpose a salt of the active ingredient is dissolved in a 0.72% aqueous sodium chloride solution and the pH of the solution is adjusted to 5.

The process according to the invention is further illustrated by the following examples which are not intended to limit the scope of the invention in any way.

EXAMPLE 1

17,18-Dehydro-apovincamine 13.4 g (38 mmoles) of a 1:1 mixture of a 1:1 mixture of 17,18-dehydro-vincamine and 17,18-dehydro-14-epivincamine is dissolved in 200 ml. of dry chloroform. To the solution 20 g. of dry formic acid and 11.3 g. of acetyl chloride are added and the reaction mixture is allowed to stand for 2 hours. The mixture is then diluted with 200 ml. of chloroform whereupon it is shaken with 550 ml., ice-cooled 1 N aqueous sodium hydroxide solution and subsequently 100 ml. of water. The organic phase is dried on sodium sulfate, filtered and the filtrate is evaporated to dryness. 11.9 g. (35.6 mmoles) of the named compound are obtained, melting at 110° to 112° C. after recrystallization from ethanol.

$[\alpha]_D^{20} = +143°$ (c=1, chloroform).

Formula: $C_{21}H_{22}O_2N_2$ (molecular weight: 334).

The same procedure is followed and the end product is obtained practically with the same yield if pure 17,18-dehydro-vincamine or the 14-epimer thereof is employed as a starting compound.

EXAMPLE 2

17,18-Dehydro-apovincaminol

A solution of 5.5 g. (16,5 mmoles) of 17,18-dehydro-apovincamine in 200 ml. of absolute diethyl ether are added to 5 g. of lithiumaluminum hydride in 300 ml. of absolute diethyl ether dropwise, whereupon the reaction mixture is boiled for one and a half hours. The excess of the reducing agent is then decomposed with water carefully, the mixture is shaken with water, the ethereal phase is dried on sodium sulfate, filtered and the filtrate is evaporated. The evaporation residue is recrystallized from 25 ml. of ethanol to yield 4.8 g. (95%) of the title compound, melting at 156° to 166° C.

$[\alpha]_D^{20} = -26°$ (c=1, chloroform)

Formula: $C_{20}H_{22}ON_2$ (molecular weight: 306).

EXAMPLE 3

17,18-Dehydro-apovincaminol-3',4',5'-trimethoxy-benzoate

To a solution of 10 g. (32.7 mmoles) of 17,18-dehydro-apovincaminol in 200 ml. of absolute benzene 12 ml. of absolute pyridine and 11.2 g. (48 mmoles) of 3,4,5-trimethoxy-benzoyl chloride are added. The reaction mixture is kept at 40° C. for one and a half hours, and is then diluted with 200 ml. of benzene. The reaction mixture is shaken with 120 ml. of ice-cooled, 1 N aqueous sodium hydroxide solution and subsequently with 50 ml. of water, the organic phase is dried on sodium solfate, filtered and the filtrate is decolored by passing through a column filled with alumina. By evaporation of the decolored solution 13.2 g. (80%) of the named compound are obtained, melting at 138° to 140° C. after recrystallization from ethanol.

$[\alpha]_D^{20} = +31.5°$ (c=1, chloroform).

Formula: $C_{30}H_{32}O_5N_2$ (M=500).

EXAMPLE 4

17,18-Dehydro-apovincaminol-3',4',5'-trimethoxy-benzoate hydrogentartarate

The product of Example 3 is dissolved in ethanol and a solution of D-tartaric acid is added until the precipitation of salt is complete.

The named compound is obtained, melting at 110° to 112° C. (decomp.).

Analysis for $C_{34}H_{38}O_{11}N_2$ (molecular weight: 650): Calculated: N 4.3%; Found: N 4.24%.

U.V. spectrum$_{max}$:209, 251, 304, 315 nm.

EXAMPLE 5

The preparation of creams

| | |
|---|---|
| 17,18-dehydro-apovincaminol-3',4',5'-trimethoxy-benzoate | 2 g. |
| propylene glycol | 50 g. |
| paraffin oil | 26 g. |
| polyethylene glycol 400 | 5 g. |
| stearyl alcohol | 15 g. |
| glycerol monostearate | 2 g. |

The active ingredient is dissolved in propylene glycol on a water bath the temperature of which does not exceed 50° C. The other components are heated up to melt, whereupon are cooled to 40° to 45° C. under stirring. To the melt the solution of active ingredient is added under stirring and the cream obtained is stirred until it is cooled down.

Creams containing 0.25%, 0.5, 1.0 and 1.5% of active ingredient can be prepared in an analogous way.

EXAMPLE 6

| | |
|---|---|
| 17,18-dehydro-apovincaminol-3',4',5'-trimethoxy-benzoate | 1.0 g. |
| triamcinolon acetonide | 0.1 g. |
| propylene glycol | 50.9 g. |
| paraffine oil | 26.0 g. |
| polyethylene glycol 400 | 5.0 g. |
| stearyl alcohol | 15.0 g. |
| glycerol monostearate | 2.0 g. |

The procedure described in Example 5 is followed except that two active ingredients are dissolved in propylene glycol.

EXAMPLE 7

| | |
|---|---|
| 17,18-dehydro-apovincaminol-3',4',5'-trimethoxy benzoate | 0.25% |
| triamcinolon acetonide | 0.1% |
| propylene glycol | 30.0% |
| 96% ethanol | ad 100.0% |

A tincture is prepared by mixing the ingredients listed above.

EXAMPLE 8

| | |
|---|---|
| 17,18-dehydro-apovincaminol-3',4',5'-trimethoxy benzoate | 0.25% |
| cetostearyl alcohol | 1.0% |
| benzyl alcohol | 2.0% |
| polyoxyethylene sorbitane monostearate | 15.0% |
| 96% ethanol | 30.0% |
| focon | 20.0% |
| distilled water | ad 100.0% |

An aerosol foam is prepared using the above ingredients.

We claim:

1. 17,18-Dehydro-apovincaminol-3',4',5'-trimethoxy-benzoate or a pharmaceutically acceptable acid addition salt thereof.

2. A pharmaceutical composition for treating psoriasis which comprises as active ingredient a pharmaceutically effective amount of 17,18-dehydro-apovincaminol-3',4',5'-trimethoxy-benzoate or a pharmaceutically acceptable acid addition salt thereof in combination with at least one pharmaceutically inert carrier or diluent.

3. A pharmaceutical composition as claimed in claim 2 which comprises 0.1 to 8.0% by weight, of 17,18-dehydro-apovincamino-3',4',5'-trimethoxy-benzoate or a pharmaceutically acceptable acid addition salt thereof.

4. A method of treating psoriasis which comprises the steps of applying to the skin a composition containing a pharmaceutically effective amount of 17,18-dehydro-apovincaminol-3',4',5'-trimethoxy-benzoate or a pharmaceutically acceptable acid addition salt thereof.

5. A method as claimed in claim 4 which comprises employing the composition as a cream, ointment, solution, aerosol, aerosol foam or injection suitable for subcutaneous or intracutaneous administration.

6. 17,18-Dehydro-apovincaminol.

* * * * *